US006068835A

United States Patent [19]

Franzke et al.

[11] Patent Number: 6,068,835

[45] Date of Patent: May 30, 2000

[54] COSMETIC COMPOSITIONS FOR HAIR TREATMENT CONTAINING DENDRIMERS OR DENDRIMER CONJUGATES

[75] Inventors: Michael Franzke, Rossdorf-Gundernhausen; Karin Steinbrecht, Ober-Ramstadt; Thomas Clausen, Alsbach; Sabine Baecker, Rüsselsheim; Jürgen Titze, Gross-Bieberau, all of Germany

[73] Assignee: Wella Aktiengesellschaft, Darmstadt, Germany

[21] Appl. No.: 08/883,924

[22] Filed: Jun. 27, 1997

[30] Foreign Application Priority Data

Jun. 28, 1996 [DE] Germany ........................... 196 25 928

[51] Int. Cl.[7] ........................................ A61K 7/11

[52] U.S. Cl. ......................... 424/70.11; 424/47; 424/701; 424/705; 424/401; 424/DIG. 16; 424/DIG. 1

[58] Field of Search ................................... 424/401, 70.1, 424/DIG. 16, 70.2, DIG. 1, 70.5, 70.11, 47; 514/944

[56] References Cited

U.S. PATENT DOCUMENTS

| | | | |
|---|---|---|---|
| 4,036,808 | 7/1977 | Rembaum et al. . | |
| 4,102,827 | 7/1978 | Rembaum et al. . | |
| 4,558,120 | 12/1985 | Tomalia et al. . | |
| 4,587,329 | 5/1986 | Tomalia et al. . | |
| 5,210,309 | 5/1993 | Newkome et al. . | |
| 5,449,519 | 9/1995 | Wolf et al. | 424/401 |
| 5,658,574 | 8/1997 | Bahary et al. | 424/400 |

FOREIGN PATENT DOCUMENTS

| | | |
|---|---|---|
| 0271180B1 | 5/1993 | European Pat. Off. . |
| WO92/14543 | 9/1992 | WIPO . |
| WO93/21144 | 10/1993 | WIPO . |

*Primary Examiner*—Jyothsna Venkat
*Attorney, Agent, or Firm*—Michael J. Striker

[57] ABSTRACT

The hair treatment compositions are in a variety of forms including permanent shaping compositions, oxidative after-treatment compositions, hair fixing compositions, hair bleaching compositions, hair cleansing compositions, hair care compositions or hair dye compositions containing direct-dyeing dye compounds and/or a combination of at least one developer and coupler and are characterized by 0.1 to 35 percent by weight of at least one dendrimer, preferably a poly(iminopropane-1,3-diyl)-dendrimer with nitrile and/or amino end groups. Methods of hair treatment based on these hair treatment compositions are described.

4 Claims, No Drawings

COSMETIC COMPOSITIONS FOR HAIR TREATMENT CONTAINING DENDRIMERS OR DENDRIMER CONJUGATES

BACKGROUND OF THE INVENTION

The present invention relates to a cosmetic composition for hair treatment with a content of at least one dendrimer or dendrimer conjugate.

A pleasing outer appearance has always been viewed as very important. Hair styling plays a special roll in providing that pleasing outer appearance. Well cared for hair is the basis for a pleasing hair style. An entire series of hair treatment compositions, such as shampoos, hair care preparations, rinses, sprayed liquid, which are applied in the widest variety of types of applications, e.g. as leave on- or rinse off-products, exists for the care and cleaning of the hair. Besides these hair care products three additional product categories are used for modifying the hair, namely permanent or temporary hair dye compositions, permanent hair shaping compositions in the form of mildly alkaline or acidic permanent wave and hair curling compositions and compositions that allow only a temporary shaping and stabilizing of the hair-do and are generally known as styling compositions. These products include hair sprays, hair lacquers, fixing lotions, fixing foams, hair gels, luster-providing products, hair creams, etc. All these agents or compositions usually contain a plurality of individual ingredients or components that fulfill a wide variety of purposes in the concerned recipe.

Thus substances were sought which are compatible in the largest possible number of recipes and which can perform a variety of functions according to the formulation. Substances which can perform two or more functions in a recipe are of special interest. The requirements for hair care include, for example, that wet hair should already have a good, pleasant feel and a good combability. A pleasant feel elasticity and volume (with the exception of "Wetlook" hair-dos) are similarly expected of dry hair.

SUMMARY OF THE INVENTION

It is an object of the present invention to find a new class of substances which fulfill the above-named requirements.

According to the invention one such new class of substances are the starburst dendrimers described in the following disclosure. Dendrimers are useful in all types of hair treatment compositions.

Indeed the low molecular weight dendrimers cause a definite reduction in wet combing force and provide a good feel in acid media. The dry hair treated in this way has good volume and elasticity.

The subject matter of the invention is thus a cosmetic composition for hair treatment with a content of at least one dendrimer or dendrimer conjugate in a suitable cosmetic foundation or base.

Dendrimers are three-dimensional, highly branched oligomers and polymers with a well defined chemical structure. Generally dendrimers comprise a core made from a plurality of branches, the so-called generations, and end groups.

Dendrimers are described in a number of patent applications. Thus building blocks made from dendrimers are described in U.S. Pat. No. 5,210,309. U.S. Pat. No. 4,102,827 and U.S. Pat. No. 4,036,808 describe making highly cationic polyelectrolytes in the form of branched polyelectrolytes or star-shaped polyelectrolytes and the use of such cationic electrolytes in conductive hydrogels. WO 93/21144 describes the production of cascade polymers. A series of applications describe the making of dendrimers and applications for pharmaceutical purposes. In EP 0 271 180 star-shaped conjugates for pharmaceutical and agricultural purposes are described. In SE 468 771 the making of polyester dendrimers and their uses as coupling components in polyester, epoxy- or polyurethane resins and their use as binder components for a series of non-cosmetic applications is claimed. WO 92/14543 describes unimolecular micelles based on cascade polymers and methods of making them. In U.S. Pat. No. 4,587,329 and U.S. Pat. No. 4,558,120 a method of making star-shaped dendrimers and their application as demulsifiers in O/W emulsions is described. The use of star-shaped dendrimers for calibration and characterization of substances with an overall dimension up to 10 $\mu$m is claimed in EP 0 247 629. A series of scientific publications disclosing methods for making dendrimers exists in addition to the above-described patents. Dendrimers can be made in very different ways. They can be made according to the methods described in WO 93/21144 or EP 0 271 180. Additional manufacturing processes are described in U.S. Pat. No. 4,587,329, U.S. Pat. No. 4,558,120 and WO 92/14543. Furthermore a series of additional disclosures exist in which the making of dendrimers is described.

The preferred dendrimers in the cosmetic compositions according to the invention are made from a 1,4-diaminobutane core by a stepwise Michael Addition of acrylnitrile with subsequent catalytic hydrogenation of the cyano groups to amino groups, in which dendrimers with nitrile or amino end groups are obtained. These dendrimers are designated as poly(iminopropan-1,3-diyl)dendrimer with nitrile and/or amino end groups. Suitable dendrimers are, e.g., marketed under the tradename 4-cascade: 1,4-diaminobutane [4]: propylamine and/or x-cascade: 1,4-diaminobutane [4]: (1-azabutylidene)$^{x-4}$: propylamine by DSM/Netherlands, wherein x=4, 8, 16, 32 or 64.

The cosmetic composition according to the invention preferably contains from 0.01 to 75 percent by weight, especially preferably from 0.1 to 35 percent by weight, of the at least one dendrimer or dendrimer conjugate. The composition according to the invention can be in the form of a hair wash composition, a hair care composition, a hair fixing composition, a hair dye composition or a hair tinting composition. The composition can be applied as a lotion, foam, milk, gel, cream, gel foam or spray. It can be formulated as a leave-on or as a rinse-off product.

The cosmetic composition according to the invention can furthermore contain standard conventional cosmetic additives for hair treatment compositions, for example, solvents, such as water and lower aliphatic alcohols, e.g. ethanol, propanol and isopropanol, or glycols, such as glycerol and 1,2-propylene glycol; wetting agents or emulsifiers from the classes of anionic, cationic, amphoteric or non-ionic surface active substances or surfactants, such as fatty alcohol sulfates, alkylbenzene sulfonates, alkyltrimethylammonium salts, alkylbetaines, ethoxylated fatty alcohols, ethoxylated nonylphenols, fatty acid alkanol amides, ethoxylated fatty acid esters, in an amount of from 0.1 to 30 percent by weight; perfume oils in an amount of from 0.1 to 5.0 percent by weight; turbidity-inducing agents, such as, e.g., ethylene glycol distearates, in an amount of from about 0.2 to 5.0 percent by weight; pearlescence agents, such as a mixture of fatty acid monoalkylol amides and ethylene glycol distearate, in an amount of from about 1.0 to 10 percent by weight; bactericidal and fungicidal materials, such as 2,4,4-trichloro-2-hydroxydiphenyl ether or methyl chloroisothiazoline, in an amount of from 0.01 to 1.0 percent by weight; thickeners, such as coconut oil fatty acid diethanol amide in an amount of about 0.2 to 3.0 percent by weight; buffer substances, e.g. sodium citrate or sodium phosphate, in an amount of 0.1 to 1.0 percent by weight; solubilizing agents, such as ethoxylated castor oil, in an amount of from about 0.1 to 1.0 percent by weight; dye compounds, such as fluorescein sodium salt, in an amount of from about 0.1 to 1.0 percent by weight; care-giving materials, such plant and herbal extracts, protein and silk hydrolyzates, cationic resins, lanolin derivatives, in an amount of from 0.1 to 5 percent by weight; physiologically compatible silicone derivatives, such as silicone oil, silicon polymers and siloxane; light protective agents, moisture containing agents, antioxidants, radical-trapping agents, anti-flaking agents, in an amount of from about 0.1 to 2 percent by weight; physiologically compatible organic or inorganic acids, such as formic acid, glyoxylic acid, lactic acid, tartaric acid, citric acid or phosphoric acid; natural, modified natural or synthetic polymers, such as shellac, cationic polymers, anionic polymers, non-ionic polymers, amphoteric polymers, chitosan, chitin or chitosan derivatives; direct-dyeing hair dye compounds, which are developed by oxidation, oxidizing agents, reducing agents, fatty alcohols, sheen-giving agents, vitamins, softeners, combability improving agents, defattying agents, defoaming agents and propellant gases, such as fluorinated hydrocarbons, dimethylether, hydrocarbons and compressed gases.

In a preferred embodiment of the invention the composition according to the invention also contains from 0.01 to 40 percent by weight, especially preferably from 0.01 to 25 percent by weight of at least one anionic, cationic, amphoteric or non-ionic surfactant and from 50 to 90 percent by weight water. A composition of this type can be used as a hair cleansing agent.

In a further preferred embodiment the composition according to the invention contains additionally at least one natural or synthetic polymer, which is selected from the group of fixing and thickening polymers. The polymers can be used in amounts of from 0.01 to 25 percent by weight, preferably from 0.1 to 20 percent by weight and can be present in dissolved form or as a dispersion. A composition of this type including the fixing polymers can be used as a hair fixing composition.

When the composition according to the invention is a permanent shaping composition, it contains from 0.5 to 15 percent by weight of at least one keratin-reducing mercapto compound and is present advantageously as an aqueous, alkaline or weakly acidic (pH=5 to 10) preparation, which contains as keratin-reducing mercapto compound, e.g. cysteine, cysteamine, N-acetyl-L-cysteine, mercaptocarboxylic acids, such as thioglycolic acid or thiolactic acid, or salts of mercaptocarboxylic acids, such as ammonium and guanidine salts of thioglycolic acid or thiolactic acid.

The required alkalinity is adjusted by addition of ammonia, organic amines, ammonium and alkali carbonates or alkali hydrogen carbonates. However the composition according to the invention can also be a neutral or acidic hair shaping composition (pH=4.5 to 7) which has an effective content of sulfites or mercaptocarboxylic acid esters.

In the first case advantageously sodium or ammonium sulfite or the salt of sulfuric acid with an organic amine, for example monoethanol amine and guanidine, is used in a concentration of about 2 to 12 percent by weight (calculated as $SO_2$). In the later case thioglycolic acid monoglycolic ester or -glycerol ester is used in a concentration of about 5 to 50 percent by weight (corresponding to a content of free thioglycolic acid of from 2 to 16 percent by weight).

The composition according to the invention for permanent hair shaping also can contain a mixture of the aforementioned keratin-reducing compounds.

After a sufficient acting time for permanent shaping of hair, which amounts to from about 10 to 30 minutes, according to the condition of the hair, the pH and the shaping effectiveness of the hair shaping agent as well as the application temperature, the hair is rinsed with water and subsequently oxidatively after-treated ("fixed"). The after-treatment composition, is used in an amount of from about 50 to 100 g according to the amount of the hair.

A fixing composition according to the invention with a content of dendrimers or dendrimer conjugates and any known oxidizing agent used up to now in this sort of treatment can be used for the oxidative after-treatment. For example, oxidizing agents used in this type of fixing composition include sodium and potassium bromate, sodium perborate, urea peroxide and hydrogen peroxide.

The concentration of oxidizing agent differs according to the application time (usually about 5 to 15 minutes) and the application temperature. Usually the oxidizing agent is present in the aqueous fixing composition in a concentration of from about 0.5 to 10 percent by weight.

Both the composition according to the invention for permanent shaping of hair and also the composition for fixing hair can be present in the form of an aqueous solution or emulsion and in thickened form on an aqueous basis, especially as a cream, gel or paste.

Subsequently the curlers are removed. In cases where it is required, the curled hair can be given an oxidative hair treatment. Then the hair is rinsed with water, put in a hair-do and finally dried.

The above-described process for permanent shaping of hair provides a safe and uniform shaping from the hair roots to the hair tips, an outstanding wet and dry combability, a pleasant feel and an attractive look in the dry state as well as a loose, springy and uniform permanent wave, especially in the vicinity of the hair roots.

A hair dye composition according to the invention contains also from 0.05 to 2.0 percent by weight of at least one direct-dyeing hair dye, which, for example, can be selected from the following classes of direct-dyeing hair dye compounds: aromatic nitro dye compounds, e.g., 1,4-diamino-2-nitrobenzene; azo dye compounds, for example Acid Brown 4 (C.I. 14 805); anthraquinone dye compounds, e.g. Disperse Violet 4 (C.I. 61 105); triphenylmethane dye compounds, e.g. Basic Violet 1 (C.I. 42 535), wherein these dye compounds can have an acidic, nonionic or basic character according to the type of their substituents; and/or natural hair dye compounds, such as Henna or Reng, which do not require oxidation to develop their colors.

The composition according to the invention can be sprayed using a propellant or dispensed with the help of a mechanical spraying apparatus or with the help of a foam producing apparatus as a foam.

When the cosmetic composition according to the invention is sprayed with the help of a propellant composition, it advantageously contains from 3 to 75 percent by weight of a propellant and is filled in a pressurized container.

Lower alkanes, such as n-butane, i-butane and propane or their mixtures, or also dimethyl ether and fluorinated hydrocarbons, such as F 152 (1,1-difluoroethane) or F 134 (tetrafluoroethane) and furthermore gases at the pressures which are to be used, for example, $N_2$, $N_2O$ and $CO_2$ and mixtures thereof, can be used as the propellant.

Mechanical spraying or foam producing apparatuses are those apparatuses which allow spraying or foaming of a liquid without using a propellant. For example, a spray pump or an elastic container provided with a spray valve can be used as a suitable mechanical spray apparatus. The composition according to the invention is filled in this container under pressure, so that the elastic container is expanded. The composition is continuously dispensed from the container, when the spray valve is opened, because of the contraction of the elastic container. As a suitable mechanical foam producing apparatus, e.g., the top with a foam producing device described in EP-B 0 0460 154 can be used on a flexible container.

When the cosmetic composition according to the invention is used for hair care, the following method is used.

After washing the hair from 5 to 30 g of the composition according to the invention are distributed on the hand towel dried hair, according to the amount of hair, and allowed to act on the hair for about 3 to 15 minutes. Subsequently the composition is rinsed out of the hair, the hair is combed, a hair-do is formed as needed and the hair is dried. In a preferred embodiment of the invention the composition is allowed to remain on the hair, which means that it is not rinsed out of the hair and thus saves the user some work.

The hair treatment composition according to the invention may include a bleaching agent so that it is in the form of the hair bleaching composition.

When the composition according to the invention is an oxidation hair dye composition, it contains from about 0.01 to 5.0 percent by weight of a suitable coupler substance and from about 0.01 to 5.0 percent by weight of a suitable developer substance. For example, suitable coupler substances include resorcinol, 4-chlororesorcinol, 1-naphthol, 3-aminophenol or derivatives of m-phenylene-diamines. Suitable developer substances include, e.g., 2,5-diaminotoluene, 2,5-diaminophenylethyl alcohol, p-aminophenol or 1,4-diaminobenzene. For development of the hair color a suitable oxidizing agent such as hydrogen peroxide or its addition compounds with urea, melamine, sodium borate or sodium carbonate are used in the form of a 3- to 12- percent by weight aqueous solution, however also air oxygen can be used.

The following examples should illustrate the subject matter of the present invention, but without limiting the appended claims provided hereinbelow.

EXAMPLES

Example 1: Permanent Wave Shaping Composition

| A | B | |
|---|---|---|
| 7.4g | — | 4-cascade: 1,4-diaminobutane[4]: propylamine |
| — | 10.0g | 32-cascade: 1,4-diaminobutane[4]: (1-aza-butylidene)$^{28}$: propylamine |
| 8.0g | 8.0g | thioglycolic acid |
| 2.6g | 2.6g | ammonium hydrogen carbonate |
| 0.3g | 0.3g | glycerin polyethyleneglycol-(35)-ricinate |
| 0.3g | 0.3g | perfume |
| 0.1g | 0.1g | octylphenol, ethoxylated with 20 Mol ethylene oxide |
| 81.3g | 78.7g | water |
| 100.0g | 100.0g | |
| 8.1 | 8.1 | pH value |

Example 2: Permanent Wave Shaping Composition

| | |
|---|---|
| 7.36g | 8-cascade: 1,4-diaminobutane[4]: (1-aza-butylidene)$^{4}$: propylamine |
| 7.06g | thiolactic acid |
| 2.50g | L-cysteine |
| 1.50g | Polypropylene(1)-polyethylene-(9)-lauryl glycol ether |
| 0.75g | perfume |
| 0.23g | dimethyldiallylammonium chloride |
| 80.60g | water |
| 100.0g | |
| 8.4 | pH value |

Example 3: Acidic Permanent Wave Shaping Composition

| | |
|---|---|
| 0.55g | 16-cascade: 1,4-diaminobutane[4]: (1-aza-butylidene)$^{12}$: propylamine |
| 7.28g | monothioglycolic acid glyceryl ester |
| 0.71g | DL-2-pyrrolidone-5-carboxylic acid |
| 0.60g | perfume |
| 0.50g | glycerin polyethyleneglycol-(35)-ricinate |
| 0.40g | octylphenol, ethoxylated with 20 Mol ethylene oxide |
| 0.30g | vinylpyrrolidone/methacrylamidopropyl-trimethylammonium chloride copolymer |
| 0.20g | vinylpyrrolidone/polystyrene copolymer |
| 89.46g | water |
| 100.0g | |
| 6.5 | pH value |

Example 4: Permanent Wave-Fixing Composition

| | |
|---|---|
| 0.5g | 8-cascade: 1,4-diaminobutane[4]: (1-aza-butylidene)$^{4}$: propylamine |
| 10.0g | sodium bromate |
| 3.2g | disodium hydrogen phosphate dodecahydrate |
| 0.8g | ortho-phosphoric acid (85%) |
| 0.5g | monosodium phosphate |
| 85.0g | water |
| 100.0g | |
| 6.4 | pH value |

Example 5: Foam Fixing Composition

| | |
|---|---|
| 1.15g | 4-cascade: 1,4-diaminobutane[4]: propylamine |
| 14.00g | hydrogen peroxide (35 percent) |
| 3.41g | o-phosphoric acid (85 percent) |
| 1.25g | DL-2-pyrrolidone-5-carboxylic acid |
| 0.66g | laurylaminodimethylacetobetaine |
| 0.50g | Polypropylene-(1)-polyethylene-(9)-lauryl glycol ether |
| 0.20g | perfume |
| 0.05g | p-acetainophenol |
| 78.78g | water |
| 100.0g | |
| 2.2 | pH value |

Example 6: Fixing Composition

| | |
|---|---|
| 1.02g | 32-cascade: 1,4-diaminobutane[4]: (1-aza-butylidene)$^{28}$: propylamine |
| 20.00g | hydrogen peroxide |
| 3.05g | o-phosphoric acid (85 percent) |
| 1.50g | disodiumhydrogen phosphate |
| 1.13g | cetyltrimethylammonium chloride |
| 0.45g | hydrogenated rhizonic oil, ethoxylated with |

-continued

| | |
|---|---|
| | 45 Mol ethylene oxide |
| 0.35g | DL-2-pyrrolidone-5-carboxylic acid |
| 0.30g | perfume |
| 0.05g | 1-hydroxyethylidene-1,1-diphosphoric acid |
| 72.15g | water |
| 100.0g | |
| 2.2 | pH value |

Example 7: Shampoo

| | |
|---|---|
| 0.60g | 16-cascade: 1,4-diaminobutane[4]: (1-aza-butylidene)$^{12}$: propylamine |
| 15.90g | decylpolyglucose |
| 3.00g | coconut oil fatty acid amidopropylbetaine |
| 2.45g | polyethyleneglycol-(120)-methyl-glucose dioleate |
| 0.95g | citric acid |
| 0.50g | perfume |
| 0.35g | sodium benzoate |
| 0.06g | sodium formiate |
| 76.19g | water |
| 100.0g | |
| 5.6 | pH value |

Example 8: Shampoo

| | |
|---|---|
| 0.30g | 4-cascade: 1,4-diaminobutane[4]: propylamine |
| 11.62g | lauryl ether sulfate |
| 3.00g | sodium chloride |
| 0.37g | citric acid |
| 0.20g | perfume |
| 0.06g | 1,2-dibromo-2,4-dicyanobutane |
| 87.45g | water |
| 100.0g | |
| 5.3 | pH value |

Example 9: Conditioning Shampoo

| | |
|---|---|
| 0.80g | 32-cascade: 1,4-diaminobutane[4]: (1-aza-butylidene)$^{28}$: propylamine |
| 12.00g | laurylaminodimethylacetobetaine |
| 6.40g | potassiumcocoyl-collagen hydrolyzate |
| 3.50g | coconut oil fatty acid monoethanol amide |
| 1.30g | DL-2-pyrrolidone-5-carboxylic acid |
| 0.88g | collagen hydrolyzate |
| 0.30g | perfume |
| 0.23g | citric acid |
| 0.15g | 1,2-dibromo-2,4-dicyanobutane |
| 74.44g | water |
| 100.0g | |
| 5.4 | pH value |

Example 10: Defatting Shampoo

| | |
|---|---|
| 0.50g | 4-cascade: 1,4-diaminobutane[4]: propylamine |
| 11.20g | lauryl ether sulfate |
| 5.00g | Plant Extract Extrapon Ivy of Drago, Germany |
| 3.00g | Plant Extract Extrapon Vanilla Special of Drago, Germany |
| 3.00g | coconut oil fatty acid amidopropylbetaine |
| 2.00g | sodium chloride |
| 1.70g | 1,2-propylene glycol |

-continued

| | |
|---|---|
| 1.10g | DL-2-pyrrolidone-5-carboxylic acid |
| 0.30g | p-hydroxybenzoic acid methyl ester |
| 0.15g | perfume |
| 72.05g | water |
| 100.0g | |
| 5.3 | pH value |

Example 11: Anti-flaking Shampoo

| | |
|---|---|
| 0.65g | 64-cascade: 1,4-diaminobutane[4]: (1-aza-butylidene)$^{60}$: propylamine |
| 25.00g | monocarboxymethyl-coconutimidazoline |
| 6.00g | 3-[(3-cocoamidopropyl)dimethylammonio]-2-hydroxypropane sulfonate |
| 3.00g | glyceryl stearate |
| 1.75g | polyethyleneglycol-(120)-methylglucose dioleate |
| 1.20g | formic acid |
| 1.00g | 1,2-propylene glycol |
| 0.40g | cationic hydroxyethyl cellulose |
| 0.40g | 1-hydroxy-4-methyl-6-(2,4,4-trimethylpentyl)-2(1H)-pyridone monoethanolamine salt |
| 0.30g | perfume |
| 0.15g | ethylenediaminetetracetic acid, sodium salt |
| 60.15g | water |
| 100.0g | |
| 4.9 | pH value |

Example 12: Two-in-One Shampoo

| | |
|---|---|
| 0.71g | 8-cascade: 1,4-diaminobutane[4]: (1-aza-butylidene)$^{4}$: propylamine |
| 16.52g | lauryldimethylcaroxymethylammoniumbetaine |
| 5.00g | dioxyethylenelauryl ether |
| 4.00g | Rewoderm ® 66 E 10 Surfactant of Rewo, Germany |
| 2.20g | lauric acid diethanolamide |
| 2.00g | diquaternary polydimethylsiloxane (Abil ® Quat 3272 of Goldschmidt, Germany) |
| 0.71g | formic acid |
| 0.40g | perfume |
| 0.15g | 1,2-dibromo-2,4-dicyanobutane |
| 68.31g | water |
| 100.0g | |
| 5.2 | pH value |

Example 13: Hair Care Composition

| | |
|---|---|
| 0.93g | 32-cascade: 1,4-diaminobutane[4]: (1-aza-butylidene)$^{28}$: propylamine |
| 5.00g | glycerol monodistearate |
| 4.00g | stearyl alcohol |
| 2.07g | citric acid |
| 1.13g | cetyltrimethylammonium chloride |
| 0.50g | glycerol (86 percent) |
| 0.50g | Plant Extract Extrapon Bambus ® of Drago, Germany |
| 0.30g | perfume oil |
| 85.57g | water |
| 100.00g | |
| 3.4 | pH value |

Example 14: Intense Hair Care Composition

| | |
|---|---|
| 0.60g | 64-cascade: 1,4-diaminobutane[4]: (1-aza-butylidene)$^{60}$:propylamine |

-continued

| | |
|---|---|
| 6.00g | cetylstearyl alcohol |
| 2.00g | wool fat |
| 1.50g | DL-2-pyrrolidone-5-carboxylic acid |
| 1.00g | cetyltrimethylammonium chloride |
| 0.83g | distearyldimethylammonium chloride |
| 0.60g | 1,2-propylene glycol |
| 0.20g | perfume |
| 0.18g | collagen hydrolyzate |
| 87.09g | water |
| 100.00g | |
| 3.2 | pH value |

Example 15: Hair Balm

| | |
|---|---|
| 0.50g | 16-cascade: 1,4-diaminobutane[4]: (1-aza-butylidene)$^{12}$: propylamine |
| 6.00g | glycerylstearate/polyethyleneglycol-(20)-cetearyl ether |
| 4.00g | diquaternary polydimethylsiloxane (Abil ® Quat 3272 of Goldschmidt, Germany) |
| 2.00g | cetyl alcohol |
| 1.36g | citric acid |
| 0.14g | 1,2-dibromo-2,4-dicyanobutane |
| 0.12g | perfume |
| 85.88g | water |
| 100.00g | |
| 3.5 | pH value |

Example 16: Hair Rinse

| | |
|---|---|
| 0.75g | 8-cascade: 1,4-diaminobutane[4]: (1-aza-butylidene)$^{4}$: propylamine |
| 4.00g | cetylstearyl alcohol |
| 1.36g | DL-2-pyrrolidone-5-carboxylic acid |
| 0.75g | cetyltrimethylammonium chloride |
| 0.50g | perfume |
| 0.20g | Plant Extract Extrapon ® 5 Special of Drago, Germany |
| 92.44g | water |
| 100.00g | |
| 4.7 | pH value |

Example 17: Rinsible Hair Care Composition

| | |
|---|---|
| 0.40g | 32-cascade: 1,4-diaminobutane[4]: (1-aza-butylidene)$^{28}$: propylamine |
| 2.00g | dimethyldiallylammonium chloride |
| 1.25g | polyethyleneglyucol-(40)-sorbitan-monopalmitate |
| 1.00g | DL-2-pyrrolidone-5-carboxylic acid |
| 0.10g | perfume |
| 0.03g | cetyltrimethylammonium chloride |
| 15.00g | ethanol |
| 80.22g | water |
| 100.00g | |
| 4.2 | pH value |

Example 18: Foam-like Hair Care Composition

| | |
|---|---|
| 0.80g | 4-cascade: 1,4-diaminobutane[4]: propylamine |
| 2.00g | cationic emulsion of amine functionalized polydimethylsiloxane (929 cationic emulsion of DOW-Corning, Europe/Belgium) |
| 1.30g | citric acid |

-continued

| | |
|---|---|
| 0.50g | hydroxypropylcellulose (M = 1,150,000 g/mol) |
| 0.30g | silicone wax (2501 Cosmetic Wax of Dow-Corning, Europe/Belgium) |
| 0.20g | perfume |
| 0.25g | cetyltrimethylammonium chloride |
| 0.15g | D-panthenol |
| 0.10g | elastin hydroyzate |
| 5.00g | propane/butane (5.0 bar) |
| 10.00g | ethanol |
| 79.40g | water |
| 100.00g | |
| 5.2 | pH value |

Example 19: Hair Fixing Composition

| | |
|---|---|
| 0.40g | 32-cascade: 1,4-diaminobutane[4]: (1-aza-butylidene)$^{28}$: propylamine |
| 3.00g | vinylpyrrolidone/vinyl acetate copolymer |
| 0.90g | formic acid |
| 0.20g | 1,2-propylene glycol |
| 0.15g | perfume |
| 0.03g | cetyltrimethylammonium chloride |
| 20.00g | water |
| 75.22g | ethanol |
| 100.00g | |
| 4.7 | pH value |

Example 20: UV-Protective Lotion

| | |
|---|---|
| 0.60g | 16-cascade: 1,4-diaminobutane[4]: (1-aza-butylidene)$^{12}$: propylamine |
| 2.15g | DL-2-pyrrolidone-5-carboxylic acid |
| 1.50g | vinylpyrrolidone/vinylacetate copolymer |
| 1.25g | vinylpyrrolidone/dimethylaminoethyl-methacrylate copolymer |
| 0.20g | perfume |
| 0.15g | glycerol (85 percent) |
| 0.10g | 2-hydroxy-4-methoxybenzophenone |
| 42.80g | water |
| 51.25g | ethanol |
| 100.00g | |
| 4.3 | pH |

Example 21: Hair Care Fixing Lotion

| | |
|---|---|
| 0.75g | 64-cascade: 1,4-diaminobutane[4]: (1-aza-butylidene)$^{60}$: propylamine |
| 4.00g | vinylpyrrolidone/vinyl acetate copolymer |
| 1.20g | DL-2-pyrrolidone-5-carboxylic acid |
| 0.40g | hydrogenated rhizonic oil, ethoxylated with 40 Mol ethyleneoxide |
| 0.20g | perfume |
| 93.45g | water |
| 100.00g | |
| 3.8 | pH value |

Example 22: Foam Fixing Composition for Strong Fixing

| | |
|---|---|
| 0.30g | 64-cascade: 1,4-diaminobutane[4]: (1-aza-butylidene)$^{60}$: propylamine |
| 5.00g | vinylpyrrolidone/vinyl acetate copolymer |
| 0.60g | DL-2-pyrrolidone-5-carboxylic acid |
| 0.45g | glyceryl laurate |
| 0.15g | perfume |
| 0.06g | cetyltrimethylammonium chloride |

-continued

| | |
|---|---|
| 5.00g | propane/butane (5.0 bar) |
| 10.00g | ethanol |
| 78.44g | water |
| 100.00g | |
| 3.8 | pH value |

Example 23: Foam Fixing Composition

| | |
|---|---|
| 0.60g | 8-cascade: 1,4-diaminobutane[4]: (1-aza-butylidene)$^4$: propylamine |
| 1.80g | chitosan |
| 1.10g | formic acid |
| 0.20g | 1,2-propylene glycol |
| 0.20g | perfume |
| 0.10g | cetyltrimethylammonium chloride |
| 6.00g | propane/butane (5.0 bar) |
| 10.00g | ethanol |
| 80.00g | water |
| 100.00g | |
| 4.1 | pH value |

Example 24: Foam Fixing Composition

| | |
|---|---|
| 0.70g | 16-cascade: 1,4-diaminobutane[4]: (1-aza-butylidene)$^{12}$: propylamine |
| 3.15g | polyvinylpyrrolidone |
| 1.60g | citric acid |
| 0.60g | hydrogenated rhizonic oil, ethoxylated with 45 Mol ethylene oxide |
| 0.22g | decylpolyglucoside |
| 0.20g | vinylpyrrolidone/methacrylamidopropyl-trimethylammonium chloride copolymer |
| 0.20g | perfume |
| 6.00g | propane/butane (5.0 g) |
| 87.33g | water |
| 100.00g | |
| 3.7 | pH value |

Example 25: Porous Foam Fixing Composition

| | |
|---|---|
| 0.50g | 4-cascade: 1,4-diaminobutane[4]: propylamine |
| 2.20g | vinylimidazolium methochloride/1-vinyl-2-pyrrolidone copolymer |
| 1.00g | glucose syrup |
| 0.70g | oleylpolyethylene glycol-(200)-ether |
| 0.60g | citric acid |
| 0.10g | perfume |
| 7.00g | propane/butane (5.0 bar) |
| 10.00g | ethanol |
| 77.90g | water |
| 100.00g | |
| 6.3 | pH value |

Example 26: Care-providing Foam Fixing Composition

| | |
|---|---|
| 0.8g | 32-cascade: 1,4-diaminobutane[4].: (1-aza-butylidene)$^{28}$: propylamine |
| 6.0g | vinylcaprolactam/vinylpyrrolidone/dimethyl-aminoethylmetacrylate terpolymer |
| 0.6g | formic acid |
| 0.2g | cetyltrimethylammonium chloride |
| 0.2g | hydrogenated rhizonic oil, ethoxylated with 45 Mol ethylene oxide |

-continued

| | |
|---|---|
| 0.2g | perfume |
| 92.0g | water |
| 100.00g | |
| 4.4 | pH value |

The above composition is filled in a ratio of 94:6 with a propane-butane-propellant gas mixture.

Example 27: Dyeing and Fixing Composition

| | |
|---|---|
| 0.23g | 8-cascade: 1,4-diaminobutane[4]: (1-aza-butylidene)$^4$: propylamine |
| 2.50g | vinyl acetate/crotonic acid/polyglycol copolymer |
| 0.20g | perfume |
| 0.07g | 1-amino-4-(2',3'-dehydroxypropyl) amino-5-chloro-2-nitrobenzene |
| 0.05g | Basic Brown 17(C.I. 12 251) |
| 0.01g | Basic Blue 7(C.I. 42 595) |
| 0.0023g | Basic Violet 14 (C.I. 42 510) |
| 46.94g | water |
| 50.00g | ethanol |
| 100.00g | |
| 8.1 | pH value |

Example 28: Hair Spray with Strong Fixing Effect

| | |
|---|---|
| 0.30g | 4-cascade: 1,4-diaminobutane[4]: propylamine |
| 5.00g | t-octylacrylamide/acrylic acid/t-butyl-aminoethylmethacrylate terpolymer |
| 0.58g | 2-amino-2-methyl-1-propanol |
| 0.15g | perfume |
| 40.00g | 1,1-difluroethane |
| 53.97g | ethanol |
| 100.0g | |
| 9.0 | pH value (diluted with water 1:1) |

Example 29: Hair Spray

| | |
|---|---|
| 0.55 g | 4-cascade: 1,4-diaminobutane[4]: propylamine |
| 3.50 g | vinyl acetate/crotonic acid/polyglycol copolymer |
| 0.15 g | perfume |
| 0.14 g | formic acid |
| 45.00 g | 1,1-difluroethane |
| 50.66 g | ethanol |
| 100.0 g | |
| 8.1 | pH value (diluted with water 1:1) |

Example 30: Hair Styling Spray

| | |
|---|---|
| 0.40 g | 32-cascade: 1,4-diaminobutane[4]: (1-aza-butylidene)$^{28}$: propylamine |
| 6.50 g | vinyl pyrrolidone/vinyl acetate copolymer |
| 0.17 g | formic acid |
| 0.10 g | perfume |
| 10.67 g | butane(1.5 bar) |

-continued

| | | |
|---|---|---|
| 33.33 | g | 1,1-difluroethane |
| 42.83 | g | ethanol |
| 100.0 | g | |
| 7.1 | | pH value (diluted with water 1:1) |

Example 31: 80% VOC Hair spray

| | | |
|---|---|---|
| 0.20 | g | 4-cascade: 1,4-diaminobutane[4]: propylamine |
| 4.00 | g | t-butylacrylate/ethylacrylate/methacrylic acid terpolymer |
| 0.72 | g | 2-amino-2-methyl-1-propanol |
| 0.20 | g | cyclo-tetra(dimethylsiloxane) |
| 0.05 | g | perfume |
| 15.00 | g | water |
| 39.83 | g | ethanol |
| 40.00 | g | dimethylether |
| 100.0 | g | |
| 9.1 | | pH value (diluted with water 1:1) |

Example 32: Pump Hair Spray

| | | |
|---|---|---|
| 0.27 | g | 4-cascade: 1,4-diaminobutane[4]: propylamine |
| 4.50 | g | t-octylacrylamide/acrylic acid/t-butyl-aminoethylmethacrylate terpolymer |
| 0.52 | g | 2-amino-2-methyl-1-propanol |
| 0.30 | g | perfume |
| 0.10 | g | dimethylsiloxane/ethylene glycol copolymer |
| 6.31 | g | water |
| 88.00 | g | ethanol |
| 100.0 | g | |
| 8.9 | | pH value (diluted with water 1:1) |

Example 33: 80% VOC Pump Hair Spray

| | | |
|---|---|---|
| 0.60 | g | 64-cascade: 1,4-diaminobutane[4]: (1-aza-butylidene)$^{60}$:propylamine |
| 5.00 | g | vinyl pyrrolidone/vinyl acetate copolymer |
| 0.30 | g | perfume |
| 0.26 | g | formic acid |
| 13.84 | g | water |
| 80.00 | g | ethanol |
| 100.0 | g | |
| 5.7 | | pH value (diluted with water 1:1) |

Example 34: 55% VOC Pump Hair Spray

| | | |
|---|---|---|
| 0.79 | g | 8-cascade: 1,4-diaminobutane[4]: (1-aza-butylidene)$^{4}$: propylamine |
| 3.50 | g | vinyl acetate/crotonic acid copolymer |
| 0.20 | g | perfume |
| 0.28 | g | formic acid |
| 40.23 | g | water |
| 55.00 | g | ethanol |
| 100.0 | g | |
| 7.7 | | pH value |

Example 35: Hair Gel

| | | |
|---|---|---|
| 0.60 | g | 16-cascade: 1,4-diaminobutane[4]: (1-aza-butylidene)$^{12}$: propylamine |
| 2.50 | g | hydroxypropylmethyl cellulose |
| 0.80 | g | polyoxyethylene-(20)-sorbitan monopalmitate |
| 0.50 | g | polyoxyethylene-(25)-p-aminobenzoic acid |
| 0.40 | g | formic acid |
| 0.12 | g | cis-1-(3-chlorallyl)-3,5,7-triaza-1-azoniadamatane chloride |
| 0.10 | g | perfume |
| 23.00 | g | glycerol |
| 71.98 | g | water |
| 100.00 | g | |
| 5.4 | | pH value |

Example 36: Hair Styling Fixing Gel

| | | |
|---|---|---|
| 0.40 | g | 32-cascade: 1,4-diaminobutane[4]: (1-aza-butylidene)$^{28}$: propylamine |
| 2.50 | g | polyvinyl pyrrolidone |
| 2.00 | g | hydroxypropyl guar |
| 0.80 | g | hydrogenated rhizonic oil, ethoxylated with 45 Mol of ethylene oxide |
| 0.60 | g | DL-2-pyrrolidone-5-carboxylic acid |
| 0.45 | g | sodium benzoate |
| 0.30 | g | hydroxyethylcellulose |
| 0.20 | g | perfume |
| 0.09 | g | sodium formate |
| 0.05 | g | mica/titanium oxide/zinc oxide powder (Soloron ® Silver Sparkle of Merck, Germany) |
| 92.61 | g | water |
| 100.00 | g | |
| 6.6 | | pH value |

Example 37: Hair Fixing Liquid-Gel

| | | |
|---|---|---|
| 1.00 | g | 4-cascade: 1,4-diamino-butane[4]: propylamine |
| 3.00 | g | vinyl pyrrolidone/vinyl acetate copolymer |
| 1.80 | g | polyoxyethylene-(20)-sorbitan monopalmitate |
| 1.35 | g | polyethylene glycol-(45) |
| 1.05 | g | hydroxyethyl cellulose |
| 1.00 | g | citric acid |
| 0.20 | g | 1,2-dibromo-2,4-dicyanobutane |
| 0.20 | g | perfume |
| 30.40 | g | water |
| 100.00 | g | |
| 7.5 | | pH value |

Unless otherwise indicated, all percentages are percentages by weight.

Example 38: Comparative Measurements of Wet and Dry Combability

The wet combability and dry combability of hair treated with four aqueous solutions A to D according to the present invention were measured and compared with the measured wet and dry combability of hair treated with five aqueous solution containing standard hair care polymers.

Standard hair samples of the same length, each 17 cm long and 2.5 cm width, were first bleached with bleaching powder and 9 percent hydrogen peroxide solution for 30 minutes, then rinsed for two minutes, washed twice with a standard cleansing agent, rinsed again and brought to a uniform weight after drying.

After preliminary combing and adjustment to a residual moisture of 50%, 0.5 ml of each polymer solution is applied to one of the individual samples uniformly and placed in a foil pocket. After an acting time of 5 minutes, the combing forces for both wet combing and also dry combing were measured after drying the wet combed strand after the wet combing.

Table I shows the principle polymer ingredient of each tested solution and its concentration in the solution as well as the pH of the solution. Table II below shows the wet combing force and the dry combing force of each sample. The average combing force of an untreated control sample of hair amounted to 0.47N. The compositions A to D according to the invention have clearly reduced combing force results in comparison to those of the prior art.

TABLE I

Composition and Properties of Tested Solutions

| Sample | Polymer | Concentration | pH |
|---|---|---|---|
| A | 4-cascade: 1,4-diamino-butane[4]:propylamine | 1.50% | 6.0 |
| B | 4-cascade: 1,4-diamino-butane [4]: propylamine | 0.25% | 3.5 |
| C | 64-cascade: 1,4-diaminobutane[4]: (1-aza-butylidene)$^{60}$: propylamine | 0.25% | 6.0 |
| D | 64-cascade: 1,4-diaminobutane[4]: (1-aza-butylidene)$^{60}$: propylamine | 1.50% | 3.5 |
| E | Vinylpyrrolidone/dimethylamino-ethylmethacrylate copolymer | 0.25% | 6.0 |
| F | Vinylpyrrolidone/dimethylamino-ethylmethacrylate copolymer | 1.50% | 3.5 |
| G | Vinylpyrrolidone/dimethylamino-ethylmethacrylate copolymer | 0.25% | 3.5 |
| H | cationic hydroxypropyl cellulose | 1.50% | 6.0 |
| I | cationic hydroxypropyl cellulose | 0.25% | 3.5 |

TABLE II

Measured Wet and Dry Combing Force for Compositions according to the Invention and Prior Art

| Sample | Wet combing Force,N | Dry combing Force,N |
|---|---|---|
| A | 0.279 | 0.141 |
| B | 0.261 | 0.122 |
| C | 0.284 | 0.251 |
| D | 0.257 | 0.217 |
| E | 0.371 | 0.261 |
| F | 0.313 | 0.399 |
| G | 0.387 | 0.235 |
| H | 0.390 | 0.252 |
| I | 0.407 | 0.254 |

The disclosure in German Patent Application 196 25 928.7 of Jun. 28, 1996 is incorporated here by reference. This German Patent Application describes the invention described hereinabove and claimed in the claims appended herein in below and provides the basis for a claim of priority for the instant invention under 35 U.S.C. 119.

While the invention has been illustrated and described as embodied in a cosmetic composition for hair treatment with dendrimers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of treating hair comprising the steps of:

a) applying from 5 to 30 grams of a hair treatment composition to hand-towel-dried hair, according to the hair abundance, b) allowing the hair treatment composition to remain on the hair for from 3 to 15 minutes, and c) after step b), rinsing the hair treatment composition out of the hair and drying the hair;

wherein the hair treatment composition contains 0.01 to 75 percent by weight of at least one dendrimer and at least one cosmetic ingredient for hair treatment, in a cosmetic foundation or base; wherein said at least one cosmetic ingredient for hair treatment is at least one keratin-reducing mercapto compound for permanent hair shaping, at least one oxidizing agent for an oxidative after-treatment in said permanent hair shaping, at least one hair fixing polymer, at least one hair bleaching agent, at least one direct-dyeing hair dye compound, or a combination of at least one coupler substance and at least one developer substance for oxidative hair dyeing.

2. A method of treating hair comprising the steps of:

a) applying from 5 to 30 grams of a hair treatment composition to hand-towel-dried hair, according to the hair abundance, and b) allowing the hair treatment composition to remain on the hair;

wherein the hair treatment composition contains 0.01 to 75 percent by weight of at least one dendrimer and at least one cosmetic ingredient selected from the group consisting of hair care-giving materials and hair fixing compounds.

3. A method of cleansing hair comprising the steps of:

a) applying from 5 to 30 grams of a hair cleansing composition to hand-towel-dried hair, according to the hair abundance, b) allowing the hair cleansing composition to remain on the hair for from 3 to 15 minutes, and c) after step b), rinsing the hair treatment composition out of the hair and drying the hair; and wherein the hair cleansing composition contains 50 to 90 percent by weight water, 0.01 to 25 percent by weight of at least one anionic, cationic, amphoteric or non-ionic surfactant, and 0.1 to 35 percent by weight of at least one dendrimer, in a cosmetic base or foundation, and wherein said at least one dendrimer is a poly (iminopropane-1,3-diyl)-dendrimer with nitrile and/or amino end groups.

4. A method of treating hair comprising the steps of:

a) applying from 5 to 30 grams of a hair treatment composition to hand-towel-dried hair, according to the hair abundance, b) allowing the hair treatment composition to act on the hair for from 3 to 15 minutes, and c) rinsing the hair treatment composition from the hair;

wherein the hair treatment composition contains 0.01 to 75 percent by weight of at least one dendrimer and at least one cosmetic ingredient selected from the group consisting of hair care-giving materials and hair fixing compounds.

* * * * *